United States Patent
Boren et al.

(10) Patent No.: US 8,986,947 B2
(45) Date of Patent: Mar. 24, 2015

(54) STABILIZATION METHOD FOR BIOLOGICAL SAMPLES BY COMBINATION OF HEATING AND CHEMICAL FIXATION

(75) Inventors: Mats Boren, Uppsala (SE); Karl Skold, Uppsala (SE); Marcus Soderquist, Uppsala (SE)

(73) Assignee: Denator Aktiebolag, Gothenburg (SE)

( * ) Notice: Subject to any disclaimer, the term of this patent is extended or adjusted under 35 U.S.C. 154(b) by 0 days.

(21) Appl. No.: 13/377,944

(22) PCT Filed: Jun. 8, 2010

(86) PCT No.: PCT/SE2010/050633
§ 371 (c)(1),
(2), (4) Date: Jan. 17, 2012

(87) PCT Pub. No.: WO2011/014108
PCT Pub. Date: Feb. 3, 2011

(65) Prior Publication Data
US 2012/0122150 A1    May 17, 2012

(30) Foreign Application Priority Data
Jul. 30, 2009    (SE) .................................. 0950572

(51) Int. Cl.
*G01N 1/30* (2006.01)
*G01N 1/44* (2006.01)
(52) U.S. Cl.
CPC ... *G01N 1/30* (2013.01); *G01N 1/44* (2013.01)
USPC ...................................................... 435/40.5
(58) Field of Classification Search
CPC .................................. G01N 1/30; G01N 1/44
USPC ...................................................... 435/40.5
See application file for complete search history.

(56) References Cited

U.S. PATENT DOCUMENTS

2007/0048877 A1* 3/2007 Skold et al. ................... 436/174

FOREIGN PATENT DOCUMENTS

WO    2007024185 A1    3/2007

OTHER PUBLICATIONS

Kiernan, "Formaldehyde, formalin, paraformaldehyde, and glutaraldehyde: what they are and what they do." (2000) Microscopy Today, 1, p. 8-12.*
Kok et al. "Effect of Heating on Pulmonary Veins" (2003) Journal of Electrocardiology Physiology, vol. 14: 250-254.*
Bruce et al. "Discrepancies Between Catheter Tip and Tissue Temperature in Cooled-Tip Ablation: Relevance to Guiding Left Atrial Ablation" (2005) Circulation vol. 112: 954-960.*
Whitaker & Puigserver "Fundamentals and Applications of Enzymatic Modifications of Proteins: An Overview" (1982) In Modification of Proteins, Freeney R. et al. Advances in Chemistry: American Chemical Society: 57-87.*
International Search Report and Written Opinion (mailed Nov. 4, 2010), Second Written Opinion (mailed Oct. 17, 2011), and International Preliminary Report on Patentability (completed Nov. 28, 2011).
Boon et al., Formaldehyde fixation and microwave irradiation, The Histochemical Journal, 1988, vol. 20, nr 6-7, pp. 313-322.
Svensson et al., Heat stabilization of the tissue proteome: A new technology for improved proteomics, Journal of Proteome Research, 2009, vol. 8, nr 2, pp. 974-981.
Login et al., Rapid Primary Microwave-Aldehyde and Microwave-Osmium Fixation: Improved Detection of Rat Parotid Acinar Cell Secretory Granule alpha-Amylase Using a Post-embedding Immunogold Ultrastructural Morphometric Analysis, Journal of Histochemistry and Cytochemistry, 1995, vol. 43, nr 5, pp. 515-523.
Shiruba et al., Immunocytochemistry of formalin-fixed human brain tissues: Microwave irradiation of free-floating section, Brain research protocols, 1998, vol. 2, nr 2, pp. 109-119.
Ruijgrok et al., Optimizing glutaraldehyde crosslinking of collagen: Effects of time, temperature and concentration as measured by shrinkage temperature, Journal of Materials Science: Materials in Medicine, 1994, vol. 5, nr 2, pp. 80-87.
Login et al., A review of rapid microwave fixation technology: its expanding niche in morphologic studies, 1993, vol. 15, nr 2, pp. 58-66.
Skold et al, "A Neuroproteomoic Approach to Targeting Neuropeptides in the Brain", Proteomics, 2, 447-454, 2002.
Svensson et al., "Peptidomics-Based Discovery of Novel Neuropeptides", Proteome Res., 2, 213-219, 2003.
Theodorsson et al, "Microwave Irradiation Increases Recovery of Neuropeptides from Brain Tissues", Peptides, 11 :1191-1197, 1990.
Fox et al., "Formaldehyde fixation" J. Histochem. Cytochem. 33:845-853, 1985.
Fricker et al., "Quantitative Neuropeptidomics of Microwave-irradiated Mouse Brain and Pituitary", Molecular & Cellular Proteomics, 4:1391-1405, 2005.
Mandell, "Phosphorylation state-specific antibodies. Applications in investigative and diagnostic pathology", Am. J. Pathol. 163: 1687-1698, 2003.
Erecinska et al, "Tissue Oxygen Tension and Brain Sensitivity to Hypoxia", Respir. Physiol, 128, 3:263-276, 2001.

(Continued)

*Primary Examiner* — Jon P Weber
*Assistant Examiner* — Teresa E Knight
(74) *Attorney, Agent, or Firm* — Dentons US LLP (57) ABSTRACT

The present invention provides methods for stabilizing a biological sample for analysis. The invention more particularly provides methods combining heat treatment and chemical fixation of biological samples in order to maintain protein primary structure and post-translational modifications, such as protein phosphorylations.

25 Claims, 2 Drawing Sheets

(56) References Cited

OTHER PUBLICATIONS

Goldman et al., "Acid-induced Death in Neurons and Glia" J. Neuroscience,. 11:2489-2497, 1991.

Folbergrova et al., "Phosphorylase Alpha and Labile Metabolites During Anoxia: Correlation to Membrane Fluxes of K+ and Ca2+", J. Neurochem., 55(5): 1690-6, 1990.

Hansen, "Effect of Anoxia on Ion Distribution in the Brain", Physiol. Rev., 65, 1:101-48, 1985.

Hille, Ionic Channels in Excitable Membranes, Sinauer Associations, Sunderland, MA, 1992.

Rristian, "Metabolic Stages, Mitochondria and Calcium in Hypoxic/Ischemic Brain Damage", Cell Calcium, 36, 3-4:221-33, 2004.

Espina, et. al., "Tissue is alive: New technologies are needed to address the problems of protein biomarker pre-analytical variability," Proteomics and Clinical Applications 3, 874-882, 2009.

Goodwin RJA et al., "Stopping the clock on proteomic degradation by heat treatment at the point of tissue excision" Proteomics 10, 1751-1761, 2010.

Office Action issued in corresponding Chinese Patent Application No. 201080033940.0, Apr. 14, 2014, pp. 1-10.

* cited by examiner

STABILIZATION METHOD FOR BIOLOGICAL SAMPLES BY COMBINATION OF HEATING AND CHEMICAL FIXATION

FIELD OF THE INVENTION

The present invention relates to methods for stabilizing a biological sample for analysis. The invention more particularly relates to methods combining heating and chemical fixation of biological samples in order to maintain protein primary structure and post-translational modifications, such as protein phosphorylations.

BACKGROUND TO THE INVENTION

It is key to any analysis of a biological sample that the integrity of its constituents is conserved between the time that the sample is extracted from a living organism and the time that the analysis is carried out. Sample degradation, however, is both hard to impede, and hard to detect. The result is that many analyses are unable to detect the presence of species that have degraded long before the analysis is carried out; correspondingly, such analyses may in fact identify degradation products of critical components in place of the original components.

The assemblage of proteins in an organism is the key to understanding physiology, function and disease. Proteins are found in many different cellular compartments, for example, in cell nuclei, organelles, protoplasm, and membranes, as well as the inter-cellular space, and in body fluids such as blood. Despite their ubiquity, proteins are extremely sensitive to their environments and thus are not always easy to detect and to identify because they can degrade very quickly.

The natural functions of the assemblage of proteins in an organism are maintained by a complex but delicate balance of biochemical pathways while the organism is alive. Once an organism dies, or once a sample of tissue is extracted from a living organism, the regulatory balance of the organism or in the sample is lost and key proteins start to break down. The breakdown can manifest itself in a number of different ways. For example, some proteins whose natural role is to digest other proteins (a "proteolytic" function), and whose natural levels and activities are regulated while an organism is alive, may go out of control after death. Thus, many proteins and key polypeptides such as coactivators, hormones, and corepressors, end up being actually digested by naturally occurring proteolytic proteins in the sample. Digestion typically involves a rupturing of the polypeptide backbone at one or more points, thereby resulting in protein or peptide fragments. Still other proteins may naturally decompose by other means, such as hydrolysis; whereas in a living organism their levels are maintained because they are continually synthesized, after death they rapidly disappear. For example, post-mortem activity of proteases and oxidative stress has been shown to play an important role on peptide and protein concentration in the brain, as well as for detecting post-translational modifications (Sköld et al., "A Neuroproteomoic Approach to Targeting Neuropeptides in the Brain", Proteomics, 2, 447-454, 2002; Svensson et al., "Peptidomics-Based Discovery of Novel Neuropeptides", Proteome Res., 2, 213-219, 2003), both of which are incorporated herein by reference.

For purposes of protein identification, however, to determine what proteins are present in a sample, it is sufficient to be able to ascertain their respective primary structures, i.e., sequences. Proteins and polypeptides have been widely investigated by methods such as two dimensional gels and mass spectrometry, but such techniques depend on having access to samples in which natural protein degradation has not advanced to a point where the concentrations of critical species have been reduced below the various measurement thresholds.

Many proteins undergo natural post-translational modification as part of regulation and modification of their function and activity. Post-translational phosphorylation and de-phosphorylation of proteins is a biological process important for the regulation of cellular processes and signalling. The identification and determination of the level of protein phosphorylations is therefore of great importance for the understanding of protein function and cellular processes.

To study proteins and peptides, tissue or cell samples are usually disrupted by homogenization in certain specific buffer conditions. These buffers often contain ingredients that are supposed to cause a cessation of all protein activity, including proteins (proteases) that degrade other proteins. However, the study of tissue samples from patients or model organisms usually exposes the samples to a certain period of oxygen and nutrient depletion before homogenization and protease inactivation occurs.

Consequently, techniques have been developed in the art for attempting to preserve biological samples after extraction and prior to analysis. Examples of such techniques include tissue fixation, which typically involves immersing a sample in an aldehyde solution, and irradiating samples with microwaves (see, e.g., Theodorsson et al., "Microwave Irradiation Increases Recovery of Neuropeptides from Brain Tissues", Peptides, 11:1191-1197, 1990). Use of aldehyde solutions is problematic because it penetrates tissue slowly, ~0.5-2 allowing for degradation of macromolecules prior to complete fixation and consequently does not arrest natural degradation of proteins (Fox et al., "Formaldehyde fixation" J. Histochem. Cytochem. 33:845-853, 1985). Microwave irradiation is problematic because it is generally non-uniform, that is, some parts of the sample reach a temperature that is high enough to cause sample breakdown. Furthermore, parts of the sample can reach temperatures above 100° C. creating small holes due to steam eruptions. (See, for example, Fricker et al., "Quantitative Neuropeptidomics of Microwave-irradiated Mouse Brain and Pituitary", Molecular & Cellular Proteomics, 4:1391-1405, 2005). Furthermore, microwave irradiation has formerly been applied to living (non-human) subjects as part of a sacrificial protocol and thus has yet to be established as a tool for analyzing samples that have been extracted from subjects, both human and non-human.

WO 2007/024185 describes a method for preparing biological samples for analyses that comprises rapid and uniform heating of the sample after extraction to stop enzymatic degradation of the sample. WO 2007/024185 does not address the need for chemical fixation of samples for histological analyses. For histological analyses it is of importance to obtain fixation of the biological sample prior to submitting the sample to sectioning in order to obtain sections maintaining structures representative of the native structures of the tissue from which the sample and section are derived.

Shiurba et al. ("Immunocytochemistry of formalin-fixed human brain tissues: microwave irradiation of free-floating sections", Brain Research Protocols 2: 109-119, 1998) describe a method for preparing a biological sample for histological analysis combining formalin fixation with subsequent microwave heating. This method does not address the problems related to rapid post-sampling degradation of the sample.

Investigation of protein phosphorylation, e.g. by the use of phosphorylation state-specific antibodies, offers an important tool in investigative and diagnostic pathology. However, full benefit of the application of this technology e.g. in immunohistochemical studies is limited by the rapid loss of phosphorylation in samples before complete stabilization of the sample can be achieved (Mandell, "Phosphorylation state-specific antibodies. Applications in investigative and diagnostic pathology", Am. J. Pathol. 163: 1687-1698, 2003).

Accordingly, there is a need for reliable methods for preserving the contents and structures of tissue samples prior to analysis in a way that impedes natural degradation of the sample and that provides reliable and reproducible results.

The discussion of the background to the invention herein is included to explain the context of the invention. This is not to be taken as an admission that any of the material referred to was published, known, or part of the common general knowledge as at the priority date of any of the claims.

Throughout the description and claims of the specification the word comprise" and variations thereof, such as "comprising" and "comprises", is not intended to exclude other additives, components, integers or steps.

SUMMARY OF THE INVENTION

The present invention is based on the understanding that formalin, which is routinely used to fixate biological samples prior to analysis, penetrates tissue slowly, ~0.5-2 mm/h, allowing for degradation of macromolecules prior to complete fixation. Especially extensive changes in phosphorylation states of proteins prior to complete fixation can be demonstrated following the use of standard methods available in the art.

The present inventors have solved this problem by combining heat treatment with chemical fixation, providing an effective and reliable method for stabilizing biological samples.

Accordingly, the present invention provides a method for stabilizing a biological sample for analysis.

The method comprises:
  a) heating the sample to a temperature above 70° C. to arrest enzymatic processes; and
  b) subsequently subjecting the sample to chemical fixation.

Preferably the method is for stabilizing a biological sample for histological analysis, most preferably histochemical analysis and/or immunohistochemical analysis.

Preferably, the sample is heated to a temperature above 80° C., such as above 90° C., most preferably to a temperature above 95° C., such as to a temperature of 100° C.

Preferably, the chemical fixation is performed using a cross-linking agent. Preferably, the cross-linking agent is an aldehyde, most preferably formaldehyde or glutaraldehyde.

In one embodiment the biological sample comprises at least one protein having a post-translational modification.

In another embodiment the heating is preceded by causing a volume of the sample to adopt a shape wherein the shape permits uniform and rapid heating, thereby forming a shaped sample.

In an embodiment, the biological sample is given a shape that facilitates an effective heating in terms of the heating being uniform and fast. This helps to shorten the time needed to obtain blocking of enzymatic processes. By blocking certain enzymatic processes driven by proteins, degradation of other constituents of the sample is avoided. Because the time between taking the biological sample and performing a biological analysis has a large impact on the level of degradation, even after a short time, e.g., after as little as 1-3 minutes, it is important that heating takes place immediately after taking the sample. By heating the sample, proteins that function as enzymes lose their secondary and tertiary structure, and thereby their activity, minimizing degradation of the sample.

The methods according to the invention preserve the primary structure and post-translational modifications of proteins and peptides but simultaneously disrupts their original secondary, tertiary structures, and, where applicable, quaternary structures. The heating of the sample therefore has several advantages, including enabling species such as the relatively low-abundant neuropeptides and the more common post-translational modification of proteins that would otherwise be degraded to remain intact. In addition, the method minimizes degradation of neuropeptides and proteins in a reproducible manner. This method also makes it possible to compare the content and levels of proteins and peptides from different samples.

The present invention further provides biological samples which have been stabilized using a method according to the invention.

DETAILED DESCRIPTION OF THE INVENTION

Overview

The present invention involves methods for stabilizing a biological sample for analysis. The sample, which has been extracted from an organism, contains various macromolecules such as polypeptides or proteins. In order to stabilize the sample for analysis, the post-sampling degradation of the primary structures and post-translational modifications of the various macromolecules are arrested to the fullest extent possible.

Accordingly, in one embodiment, after a first period of time which is one over which degradation is minimal, or preferably kept at or around levels similar to those found in the sample when in vivo, the sample is rapidly and uniformly heated over a second period of time, and in such a manner that all parts of the sample reach a particular lowest temperature. The temperature is referred to as the denaturation temperature because it is a temperature at which various macromolecules denature, i.e., their secondary, tertiary, and/or quaternary structure is disrupted, but it is not a temperature at which the primary structure of the macromolecules is degraded. The denaturing temperature is preferably a temperature above 80° C., such as above 90° C., most preferably a temperature above 95° C., such as a temperature of 100° C. Preferably, the sample is not allowed to reach a temperature above 100° C.

Preferably the macromolecules that are denatured include at least those macromolecules that play a role in the natural degradation processes of the sample. For example, such macromolecules include proteolytic enzymes that, if not denatured, would degrade—e.g., by digesting—other molecules in the sample. Such macromolecules further include phosphatases, esterase, acylase, lipases, hydrolases, nucleases such as ribonucleases and deoxyribonucleases, and kinases.

It is to be understood that the conditions deployed herein lead to an effect of degree, rather than one that is absolute: it is of course understood that no chemical reaction can be halted altogether. Thus it is to be understood that, for example, although the temperatures employed are chosen to be high enough to cause denaturation and loss of enzymatic activities, but low enough not to cause degradation of primary structure of a given set of molecules, it does not mean that a small number of macromolecules do not still undergo degradation under those conditions. It is sufficient for the purposes of the present invention that the number of such macromolecules is insignificant and is, for example, less than 5% of the population of initial molecules, and is preferably less than 2%, and even more preferably less than 1%, and still more preferably less than 0.1% of the initial population of those molecules.

It is also to be understood that, when the term secondary structure is used herein, it can mean the overall three-dimensional configuration of a macromolecule that is responsible for its activity and specificity. Thus, the term secondary structure can mean herein, features of a macromolecule that are commonly referred to distinctly as secondary, tertiary, and quaternary structure.

In another embodiment, the sample is not intended to be analyzed soon after extraction but instead is intended to be stored prior to analysis. In such an embodiment, the sample is frozen as soon as is practically possible after extraction. The time between extraction and the time when the sample attains a frozen temperature is one over which degradation is minimal. The sample is caused to adopt a shape that permits rapid and uniform heating. The sample can also be caused to adopt such a shape while frozen, or prior to freezing. Then, the sample is rapidly and uniformly heated over a second period of time, and in such a manner that all parts of the sample reach the denaturation temperature. It is to be understood that the second period of time for a frozen sample is not necessarily the same as the second period of time for a sample that has not been frozen prior to heating. Preferably the second period of time is rapid so that the sample does not undergo a period of thawing in between its frozen state and the heated state. For example, rapid heating preferably occurs over less than a minute, less than 30 seconds, less than 20 seconds, less than 10 seconds, less than 5 seconds, or less than 2 seconds.

The present invention has contemplated application to analysis of polypeptides, proteins (including antibodies), carbohydrates, lipids, hormones, and metabolites in a biological sample. It would be understood, however, that study of other molecules and macromolecules may also benefit from the methods and apparatus described herein. For example, and in particular, any other macromolecules in a biological sample that have a three-dimensional conformation that may be disrupted by heating while preserving the sequence of chemical bonds within them can be preserved for analysis by the methods and apparatus described herein. Such other macromolecules include, but are not limited to, nucleic acids and oligonucleotides. Macromolecules are understood, generally, to be molecules of high molecular weight that are composed of repeating units of same or different identities. Similarly the methods of the present invention may also lead to more accurate detection of small molecules (non-macromolecules) that would otherwise be digested or degraded by other means.

The terms disrupted and degraded are used herein to refer to alteration of molecular structures in a sample. A structure is disrupted if it is altered in such a way as to impair its function, even though the structure's identity is not destroyed. Thus, a protein, for example, can be denatured and, in so doing, its secondary, and/or tertiary and/or quaternary structure is disrupted, i.e., altered so that its function is destroyed. However, such a process does not change its primary sequence and thus its identity is maintained. Conversely, a structure is degraded if its chemical identity is changed. Thus, for example, cleaving a protein to produce two or more fragments has degraded the protein because not only has its secondary and/or its tertiary and/or its quaternary structure been altered, but its primary structure has too. Another example of degradation is the loss of post-translational modifications, such as the loss of phosphorylations of proteins and peptides through the action of protein phosphatase or spontaneous hydrolysis.

The samples for use with the present invention may comprise any biological sample from an organism. Thus, the samples include, but are not limited to, tissue, muscle, bone, bone marrow, tooth, hair, skin, or any organ such as brain, kidney, liver, stomach, intestine, reproductive organs, or pancreas. The samples further include body fluids including, but not limited to tears, saliva, blood, semen, sweat, or urine.

The organism is preferably a mammal, but may be a reptile, an invertebrate, a fish, an insect, or a bird. The organism is still more preferably a human, but may be an animal, including, but not limited to: a non-human primate, rabbit, sheep, dog, cat, horse, monkey, mouse, or rat.

Exemplary Theory

While a tissue is living, proteins are synthesized and degraded. This is a dynamic process and is extensively controlled by various mechanisms. For example, proteolysis naturally occurs within living tissue but it is typically regulated so that proteins that are proteolyzed remain in sufficient quantities to perform their functions. A disease state can change this balance, and hence, a change in the balance can be used to characterize a disease.

Post-translational modification of proteins is an important means of modifying and controlling the function and activity of proteins and an important part of many cellular processes and signalling. Regulation of cellular processes by phosphorylation and de-phosphorylation of proteins by specific protein kinases and protein phosphatases is a highly dynamic process. The level of phosphorylation of specific proteins is indicative of the status of cells and tissue and therefore of great interest to investigate.

The peptidome of a sample, the set of peptides present in a specific cell, tissue, organism or system, is directly linked to its proteome. The distribution of molecules between proteome and peptidome is controlled by proteases and protease inhibitors. Post-mortem enzyme activity plays a role in the integrity of the peptide and protein content in tissues, such as brain tissue. There is always a low level of highly abundant peptides from protein degradation in a sample that arises from the natural protein-peptide homeostasis.

Many studies of tissue and cells requires their removal from the supportive environment of a living organism, thus disturbing the various regulatory processes, and in particular leading to deprivation of oxygen and nutrients in the sample, for example as blood flow to the tissue is halted. Ischemia, a restriction on blood delivery to tissue, leads to subsequent hypoxia and anoxia.

The degradation of tissue has been particularly closely studied for samples of brain tissue. Thus, even though brain cells do not contain a reservoir of oxygen in the same way that muscle cells do, i.e., with myglobin, their rate of oxygen utilization is high. To ensure brain cell survival, a constant supply of oxygen and nutrients are required. A dilemma in the study of brain tissue is that, with many types of analytical techniques, the brain tissue must be removed from its oxygen and nutrient supplying environment. Without oxygen, oxidative phosphorylation and subsequent adenosine triphosphate ("ATP") production is halted, causing deficiencies in cell functions. The time at which degradation of brain tissue begins is much shorter than the time for degradation of other biological tissues or bodily fluids. Furthermore, even within the brain, the protein and polypeptide degradation time is not uniform. Oxygen retention is generally low and non-uniform with large variation between different brain structures. It is generally higher in the regions rich in cell bodies and dendrites, such as the grey matter of the cortex, and lower in areas where fibers predominate, such as the white matter of the cortex, pons, and fornix (see, e.g., Erecinska et al., "Tissue Oxygen Tension and Brain Sensitivity to Hypoxia", Respir. Physiol., 128, 3:263-276, 2001).

Glucose is the main metabolic substrate for the adult brain. Glucose is metabolized through glycolysis to pyruvate, which enters the Krebs cycle in mitochondria where, in the presence of oxygen, it is completely oxidized to carbon dioxide and water (see, e.g., Goldman et al., "Acid-induced Death in Neurons and Glia" J. Neuroscience,. 11:2489-2497, 1991). A decrease of oxygen interferes with the conversion of pyruvate in the mitochondria. As a result, mitochondrial ATP production is compromised, leaving only glycolytic ATP production. In the ischemic brain, ATP generation occurs via anaerobic conversion of endogenous substances.

As noted, the brain contains only a paucity of oxygen stores. The stores of oxygen in blood vessels can support normal oxygen consumption in the brain for only a few seconds. Anaerobic glycolysis only yields 2 mol of ATP per mol of glucose, as compared to ~35 mol of ATP under aerobic glycolysis. This results in a utilization of endogenous stores of ATP, ADP and phosphocreatine (PCr). Creatine phosphate donates a phosphor group to ADP, thereby converting it to ATP. The high-energy phosphate compounds including creatine phosphate, are present in vitro in both neurons and glia at comparable concentrations. (See, e.g., Folbergrova et al., "Phosphorylase Alpha and Labile Metabolites During Anoxia: Correlation to Membrane Fluxes of $K^+$ and $Ca^{2+}$", J. Neurochem., 55(5): 1690-6, 1990).

By using these endogenous energy substrates, energy metabolism can be supported for approximately one minute in ischemia (Hansen, "Effect of Anoxia on Ion Distribution in the Brain", Physiol. Rev., 65, 1:101-48, 1985). In ischemia studies, glucose levels are depleted and lactate levels are 3-fold increased after 60 seconds. After 2 minutes, lactate levels are increased 5-fold (Folbergrova et al). The utilization of high-energy phosphate groups is reduced to 30% after approximately 10 seconds, 15%. after the first minute, and to nearly zero after 2 minutes (Hansen; Folbergrova, et al.).

There is an efflux of $K^+$ ions from rat brain cortex immediately after induction of anoxia through cardiac arrest (Hansen). There is a slow increase of $K^+$ ions during the first two minutes of anoxia (K-phase I). After about 2 minutes, the extracellular $K^+$ ion concentration rises from 10 mM to about 60 mM within a few seconds (K-phase II). The rapid increase in extracellular potassium takes place when the ATP energy metabolism and oxygen consumption have fallen to very low levels; between 1 and 2 minutes after ischemia. During the next few minutes the extracellular $K^+$ levels rises slowly to 80 mM (K-phase III). The slow rise during K-phase I may be due to insufficient inward pumping of $K^+$ ions due to reduced Na-K-ATPase activity. After 1 to 2 minutes of ischemia, ATP energy levels are insufficient to support Na-K-ATPase activity, causing depolarisation and a reduction of Na, K, Ca, and Cl (see, e.g., Hille, Ionic Channels in Excitable Membranes, Sinauer Associations, Sunderland, Mass., 1992).

Complete ischemia in rat cortex induces a rapid increase in intracellular Ca levels after approximately 60 seconds (Kristian, "Metabolic Stages, Mitochondria and Calcium in Hypoxic/Ischemic Brain Damage", Cell Calcium, 36, 3-4: 221-33, 2004). The ischemia-induced changes in ion homeostasis causes a depolarization, causing entry of Ca through voltage-dependent Ca-levels and NMDA-receptors. NMDA antagonist treatment of ischemic rat cortex delays the intracellular Ca increase within 30 seconds (Kristian). The Ca-ATPase activity and the Ca-sequestration into organelles is ATP driven by and therefore sensitive to the rate of energy metabolism. Increased glucose levels in rat cortex also delays Ca influx to 90 seconds (Kristian). When the energy metabolism is compromised, Ca is released from the organelles. The increase of Ca can activate K-Ca channels, thereby promoting K efflux (Hille). As the ion balance is lost, the cell organelles collapses and proteins and peptides are released and degraded.

As described, after removing a sample of tissue from a living organism, degradation increases or can continue uncontrolled, thereby rapidly leading to degradation of proteins and polypeptides within the sample. Therefore, to obtain the most information about the tissue's protein and polypeptide composition, the sample should be heated as quickly as possible after removing the sample from the organism. Without being constrained to any particular theory, it is believed that the tissue should be heated prior to the ATP levels dropping below a point that ion gradients are no longer maintained in the cells in the sample. The electrochemical gradient across a cell membrane, manifested by concentration gradients of ions such as sodium and potassium, provides a source of energy for intra-cellular chemistry. Enzymes such as $Na^+$ ATPase and $K^+$ ATPase use ATP to create and maintain such gradients. Once a cell experiences energy failure, that is, once the ATP level drops below a threshold level, calcium accumulates in the intracellular space as a result of the disturbed ion homeostasis. As the ion balance is lost, the cell organelles collapses and proteins and peptides are released and degraded.

Extraction

Extraction of a sample from an organism may take a number of forms. For example, the sample may be excised from the organism by cutting, taking a smear, or by drawing out with a syringe or a catheter.

While generally all biological samples undergo similar steps that eventually lead to necrosis, wherein ATP production and phosphorylation is halted, ion gradients are lost, the cell organelles collapse, proteins and peptides are released, and proteolysis increases, the rate of each of these steps depends at least in part on the type of sample. Thus, although massive degradation does not occur in some samples until as much as 10 minutes have elapsed, in some samples, massive degradation can occur as quickly as 3 minutes, 2 minutes, 1 minute, 30 seconds, 10 seconds or less from the time the tissue is removed from the organism. Especially loss of post-translational modifications, such as protein phosphorylations, can occur within seconds. Accordingly, the period of time between extraction of a sample from an organism and the time that the sample is heated (as further described herein) is preferably 3 minutes, still more preferably 2 minutes, and even more preferably between 10 seconds and 2 minutes. In some embodiments, to avoid degradation of the sample, the sample can be extracted by an instrument that simultaneously removes the sample and shapes the sample into the desired shape. The sample is then immediately introduced into the heating device to arrest further degradation.

Sample Shape

Determining how to shape the sample so that the sample can be uniformly heated preferably takes into account the type of device to be used to heat the sample, and various characteristics of the sample. The sample can be heated by one or more of the well-known forms of heat transfer: conduction, convection or radiation. If the sample is heated by conduction heating, a factor in determining how to choose the shape of the sample is that it is preferable that no part of the sample interior is greater than a threshold distance from a source of heat. Preferably this threshold is 5 mm, though it may vary with the nature of the tissue sample. For example, it may be 1 mm, 2 mm, 3 mm, 3.5 mm, 4 mm, 4.5 mm, 5.5 mm, 6 mm, 6.5 mm, 7 mm, 7.5 mm, 8 mm, 9 mm, or 1 cm. In some embodiments, it is preferable that the sample is shaped to have the largest surface area to volume ratio possible, such as by creating a very thin slice, preferably one that is uniformly thin. Where the heating device has conductive elements that are in specific shapes, such as a cylindrical heating element or a probe which is inserted into the sample, a cylindrical shape for the sample may be more desirable. The shape of the sample should be one that maximizes any temperature gradient that occurs across the sample during heating so that the heat conduction from the surface to the interior of the sample is as effective as possible. The speed of the heating step can be kept at a rate sufficiently fast, but also be selected to prevent the temperature from going too high, or from some parts of the sample from being heated too slowly and not being heated to the same temperature as the rest of the sample. If part of the sample is allowed to go beyond a maximum temperature, water in the sample may boil and the cell structure may be destroyed. In more extreme instances, the primary structure of a protein or polypeptide of interest may be destroyed by temperatures that are too high. Conversely, if part of the sample does not reach the denaturation temperature, the whole sample can be tainted by residual presence of the un-denatured portion. Uniform heating avoids both of these outcomes.

The sample can be shaped by cutting the sample into the desired shape. In some embodiments, the sample is pressed, or flattened, such as by applying pressure, to achieve the desired shape. In some embodiments, the sample has a thickness of between about 1 to 2,000 microns, such as between 1 and 1,000 microns, 1 and 500 microns, 1 and 200 microns, 1 and 100 microns, 1 and 50 microns, 1 and 25 microns, 1 and 20 microns, 1 and 10 microns or 1 and 5 microns. It is to be understood that the various upper and lower endpoints of the foregoing ranges may be interchanged with one another without limitation: for example, although not specifically recited hereinabove, a range of 10-50 microns is also considered within the scope of the present invention, as is 500-1,000 microns.

It is also to be understood that the term 'about' as used herein, in connection with any quantity such as a time, or a length, or a mass, is intended to mean that the value in question may vary by up to 5% smaller or larger than the quoted value. Thus, for example, a thickness of about 10 microns is intended to mean any thickness in the range 9.5 to 10.5 microns. For temperatures, the term 'about' means that a variation of ±2° C. is intended.

Freezing the Sample

Optionally, the sample can be frozen, such as by flash freezing, prior to analysis. The sample can be brought to a temperature preferably below −20° C., such as below −80° C. One advantage of freezing the sample is that the sample can be manipulated and shaped into the desired shape for uniform heating more easily when the sample is in a frozen state than when fresh. Frozen samples can be cut into thickness of less than about 5 mm, about 4 mm, about 3 mm, about 2 mm, about 1 mm or 0.5 mm. Preferably, for a frozen sample, the sample shape is a thin sheet, on the order of microns thick. Such thin slices are less easily achieved when cutting a fresh sample. The freezing solidifies any liquid in the sample, including in samples considered to be solid, and allows for more precise cutting of the sample. Additionally, freezing arrests enzymatic activity and prevents degradation of other components of the sample.

When the sample is frozen after being extracted from the organism, the sample should be kept frozen, such as below −20° C. or below −4° C. prior to heating. When a sample is frozen, ice crystals form and disturb the plasma membrane. In addition, as a frozen sample thaws, vesicle membranes become permeable. Increased permeability can cause protein degradation to occur more rapidly once the sample is thawed than in samples that have never been frozen. With some types of biological samples, the sample is not permitted to thaw before applying heat to the sample. That is, the sample is not allowed come to a temperature above −20° C. before the heat, is applied. If the sample is thawed, the sample is heated within about 30 seconds from the thawing of the sample, to prevent massive degradation from occurring.

Heating

The sample is heated, preferably uniformly, to a temperature that denatures macromolecules in the sample without degrading the primary structure of those and other macromolecules. The heating can be carried out by heat transfer from conduction, convection, or radiation. Additionally and alternatively, heating of the sample can be accomplished by directing microwave radiation on to the sample.

The sample can be heated to a temperature of about 70° C., 80° C., 90° C., 95° C., or 100° C. at normal pressure, or the boiling point of a fluid sample, depending on the type of molecule that is to be denatured. In some embodiments, the sample is prevented from being raised over a threshold temperature, such as the boiling point of the sample, or 100° C. at normal pressure, so that the primary structure is not destroyed. The sample can be heated at a higher temperature under pressure to denature the macromolecules. Maintaining the temperature of the sample below a threshold, and thereby maintaining the macrostructure, can facilitate sample analysis. If the temperature achieved by the heating step causes the sample to reach a temperature at which the secondary structure of a macromolecule is disrupted, the macromolecule is denatured. In certain instances, the heating disables enzymatic activity that degrades proteins and polypeptides. The heating can arrest at least 60%, such as at least 70%, 80%, 90% or 95% of the enzymatic activity of the sample. The heating can also alter the tertiary and secondary structure of the proteins and polypeptides of interest. However, the heating does not degrade the primary structures and post-translational modifications of macromolecules.

Any of the heating devices can heat the sample rapidly bringing all parts of the sample to a temperature least 70° C., such as in less than 2 minutes, less than 1 minute, less than 30 seconds, less than 10 seconds, less than 5 seconds, less than 2 seconds, or less than 1 second. In some embodiments, the heating brings all parts of the sample to a temperature of at least 70° C. within 2-3 minutes. Heating devices are described herein that work using conduction or radiation. Conduction heating can be used in instances where radiation will not heat a sample uniformly. In a sample that is frozen, using microwave radiation heating can cause some parts of the sample to attain the desired denaturation temperature before other parts of the sample. By way of analogy, a block of ice heated in the microwave will resist thawing, because the hydrogen bonded molecular network is not altered by the microwaves. For example, ice is thawed more efficiently by conduction than by applying microwave radiation. As the ice begins to melt in some areas, the melted ice, i.e., the water, begins to warm up and heats the surrounding ice by conduction. This can allow some parts of the ice block to thaw and reach boiling prior to other parts of the ice block thawing. This phenomenon in a biological sample causes uneven heating, which can allow for more peptide fragments to be present in the sample than would be present in a sample that is uniformly heated to the target temperature. One option for avoiding this is to thaw the sample prior to the heating step. Another option is to use a heating method other than microwave radiation for heating frozen samples. Such heating steps can avoid a separate thawing step altogether.

Timing

There are two phases after sample extraction from the organism in which the sample can degrade. The first phase begins at extraction and ends at the initiation of the heating step. The second phase beginning at the initiation of the heating step and ends when the sample reaches the desired temperature. If the sample is not frozen, the combination of the first and second phases should be completed prior to the sample degradation, i.e., prior to ion imbalance or depletion of ATP level and subsequent increased levels of molecular fragments in the sample. Described herein are methods for determining the time that applies for each type of biological sample. However, for a never-frozen sample it is desirable that the two phases are completed within 10 minutes, such as within 5 minutes, 3 minutes, 2 minutes, 1 minute, or 30 seconds. In some implementations, the second phase occurs within 2 minutes, 1 minute, 30 seconds, 20 seconds, 10 seconds, 5 seconds, 2 seconds, 1 second or less. The first phase can be both extended and shortened if the sample is frozen. The phase is extended, because the sample can be kept frozen for extended periods of time, such as days, weeks, months, or even years. However, the first phase is shortened in that the time between thawing the sample and heating the sample must be kept very short because of the acceleration of degradation that occurs after the sample is thawed.

Chemical Fixation

Chemical fixation is preferably performed in formalin, i.e. aqueous solution of formaldehyde, such as 4% formaldehyde in phosphate buffered saline. Alternatively fixation is performed in aqueous solution of glutaraldehyde, such as 2.5% glutaraldehyde in phosphate buffered saline. A suitable fixation time is normally between 6 to 36 hours.

Examples of Biological Analysis

After the samples have been stabilized using a method according to the invention, the samples can be analyzed to determine the protein and polypeptide make up of the sample. The samples can preferably be analyzed using histological methods, such as histochemical and Immunohistochemical methods.

Exemplary Devices

Regardless of whether the sample is fresh or frozen when heated, the sample can be placed in a container that can be evacuated so that the sample can contact a heat source directly, without a pocket of air between the sample and the heat source. The container can be a deformable piece of material, such as a bag or a foil, which does not release molecules that would interfere with analysis results. Suitable materials for such a container can include polymers, such as medical grade polymers, or other materials that do not give off gas, or have components that can migrate into the sample during sample handling.

The prepared samples are heated in a device that is configured for uniformly heating the sample. This allows fast and uniform heat transfer through the whole biological sample.

In some embodiments, the heat source is a single plate heated, e.g., by a heating element, and the sample, regardless of whether it is placed in a container, receives heat from one side only, i.e., there is a single contact surface allowing power to be transferred into the biological sample. In another embodiment, the heat source is a device using radiation (e.g., microwave radiation) to heat the biological. The source of radiation can be a microwave generator. Alternatively, other types of radiation can be applied to the sample, such as radiofrequency (RF) or ultrasound.

The source of radiation can output about 1 to 6 Watts of energy, such as between about 3 and 5 watts. In some embodiments, between about 2 and 4 Watts/minute/gram, such as 3.6 Watts*minute, are input into the sample to raise the temperature of the sample from 20 to 80 degrees, if the biological sample has a thermal capacity similar to water. The needed radiation energy is 3.6/efficency Watts*minutes/gram., i.e., if the efficiency is 10%, the needed radiation is 36 Watts*minutes/gram. The mass includes both the sample and the filler, i.e., if the filler has a similar mass to the sample and the sample weighs 10 grams, with an efficiency of 10% then 360 Watts are needed to heat the sample to 80 degrees in one minute. Thus, about 72 Watts are required to heat one gram at 20° C. to 80° C. in 30 seconds.

It is contemplated that any method described herein can be implemented with respect to any other method described herein.

EXAMPLES

Example 1

Immunohistochemical Visualization of the Phosphorylated Form of CREB in Samples of Mice Brain After Different Treatments Experimental
Biological Samples and Treatments Mice were sacrificed by cervical dislocation and sample collected immediately. Whole brains were excised immediately following sacrifice and were subjected whole to either of the following treatments: A: Directly submerged in 10% neutral buffered formalin (NBF), B: Kept at room temperature for 15 min prior to being submerged in NBF. C: Kept at room temperature for 2 h prior to being submerged in NBF. D: Stabilized by heat treatment in the Stabilizor T1 instrument (Denator AB, Sweden) at auto settings for fresh tissue and directly after treatment submerged in NBF.

All samples were kept for 24 h in formalin solution at room temperature prior to paraffin imbedding. All samples were incubated without further sub dissection in the NFB. Prior to paraffin embedding samples were cut into halves and embedded such that sections could be cut through the centre of the original sample.

Histochemistry

From the paraffin blocks 4 micron thick sections were cut and immediately mounted on SuperFrost Plus glass slides (BDH, Merck & Co., Inc., Poole, UK), dewaxed in xylene and rehydrated through graded alcohols to water. Sections were stained either with hematoxylin-eosin (DAKO AS, Copenhagen, Denmark) or Mallory trichrome (Bio-Optica, Milano, Italy), both according to respective manufacturers instructions without alterations.

Immunohistochemistry

From the paraffin block 4 micron thick sections were cut and immediately mounted on SuperFrost Plus glass slides (BDH, Merck & Co., Inc., Poole, UK), dewaxed in xylene and rehydrated through graded alcohols to water. Antigen retrieval was performed in a microwave oven for 10 minutes at 750 W followed by 15 minutes at 350 W in citrate buffer pH 6 (NeuN antibody, Millipore (Chemicon), #MAB377), or TE-buffer at pH 9 (pCREB(Ser133) antibody, Abcam, #ab32096) before being processed in a DAKO Autostainer Plus (DAKO AS, Copenhagen). All primary antibodies were incubated for 30 min. Immunostaining was detected with Envision Real Detection kit, Peroxidase/DAB, Rabbit/Mouse (K5007) and counter stained with hematoxylin, all according to the manufacturers instructions (DAKO AS, Copenhagen, Denmark)

Image Capture and Processing

Images were captured at 40× magnification using a ScanScope® XT digital slide scanner (Aperio Technologies Inc., Vista, Calif., USA). Subsections were selected using Aperio's ImageScope viewer and assembled into panels using Adobe PhotoShop (Adobe Systems Incorporated, San Jose, Calif., USA).

Results

Figure 1:
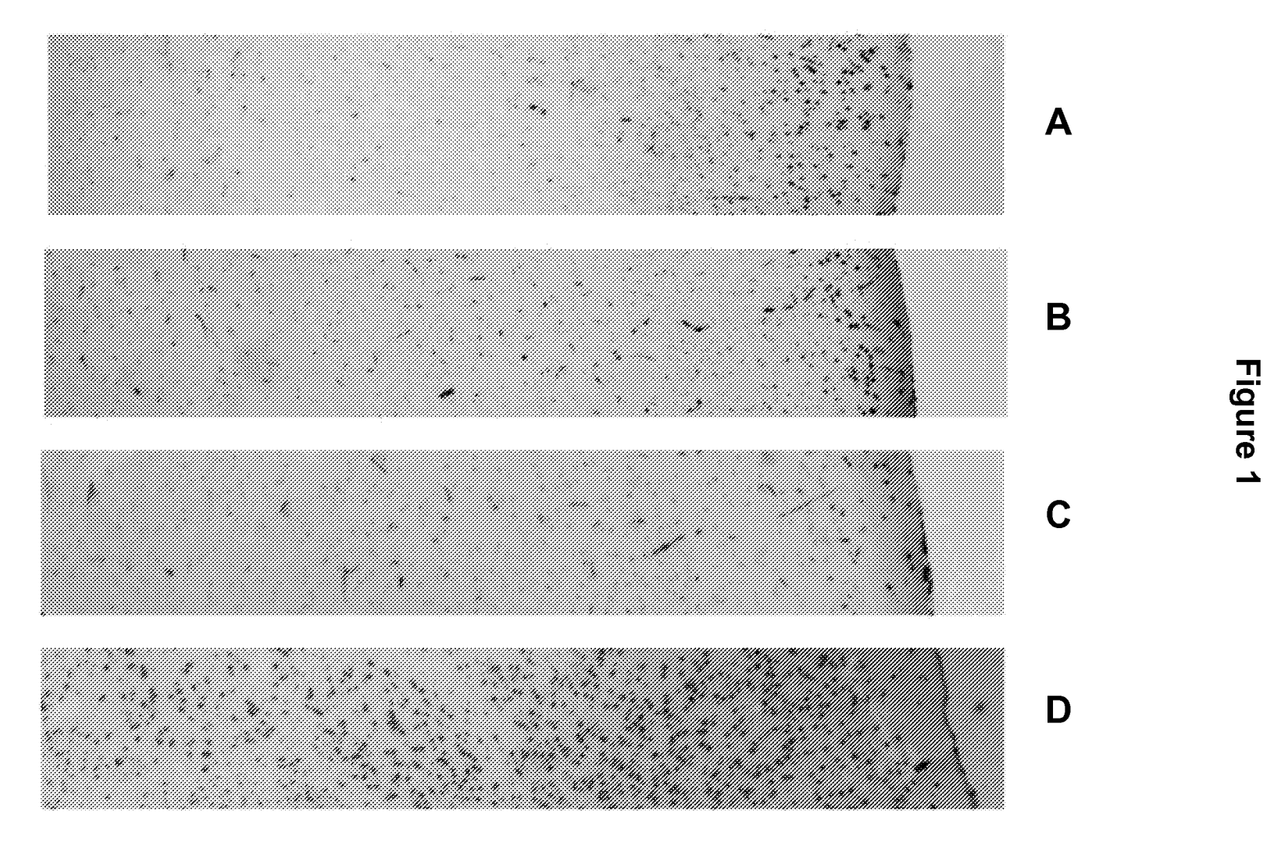
FIG. 1 shows immunohistochemical visualization of the phosphorylated form of CREB, pCREB(Ser133) in formalin fixed tissue from mouse cortex 0-120 min post mortem incubation at room temperature before submersion in formalin, Panel A 0 min, Panel B 15 min, Panel C 120 min. Panel D shows a sample treated with the method according to the invention, i.e. heating directly after extraction followed by formalin fixation.

FIG. 1 describes the results immunohistochemical visualization of the phosphorylated form of CREB, pCREB (Ser133) in formalin fixed tissue from mouse cortex 0-120 min post mortem incubation at room temperature before submersion in formalin (Panel A 0 min, Panel B 15 min, Panel C 2 h). Panel D shows a sample treated with the method according to the invention, i.e. stabilized by heat treatment directly after extraction followed by formalin fixation. Large black dots are pCREB positive nuclei and smaller gray dots are pCREB negative counter stained with Hematosin-Eosin stained. A clear gradient from outside (right) to interior (left) can be seen for 0-120 min samples evidencing degradation of pCREB. Longer post-mortem time gives shallower staining evidencing extensive degradation of pCREB. In the sample treated according to the method of the invention black large pCREB positive nuclei can be seen through out the whole sample evidencing little or no degradation of pCREB.

Example 2

Stabilization of Samples from Mice Brain

Experimental
Biological Samples and Treatments

Mice were sacrificed by cervical dislocation and sample collected immediately. Whole brains were excised immediately following sacrifice and stabilized by heat treatment in the Stabilizor T1 instrument (Denator AB, Sweden) at auto settings for fresh tissue and subsequently incubated in room temperature for the following periods of time, A: 0 min, B: 15 min, C: 6 h, and D: 24 h prior to being submerged in NBF.

All samples were kept for 24 h in formalin solution at room temperature prior to paraffin imbedding. All samples were incubated without further sub dissection in the NFB. Prior to paraffin embedding samples were cut into halves and embedded such that sections could be cut through the centre of the original sample.

Histochemistry, Immunohistochemistry, and Image capture and processing were performed as described in Example 1.

Results

Figure 2:
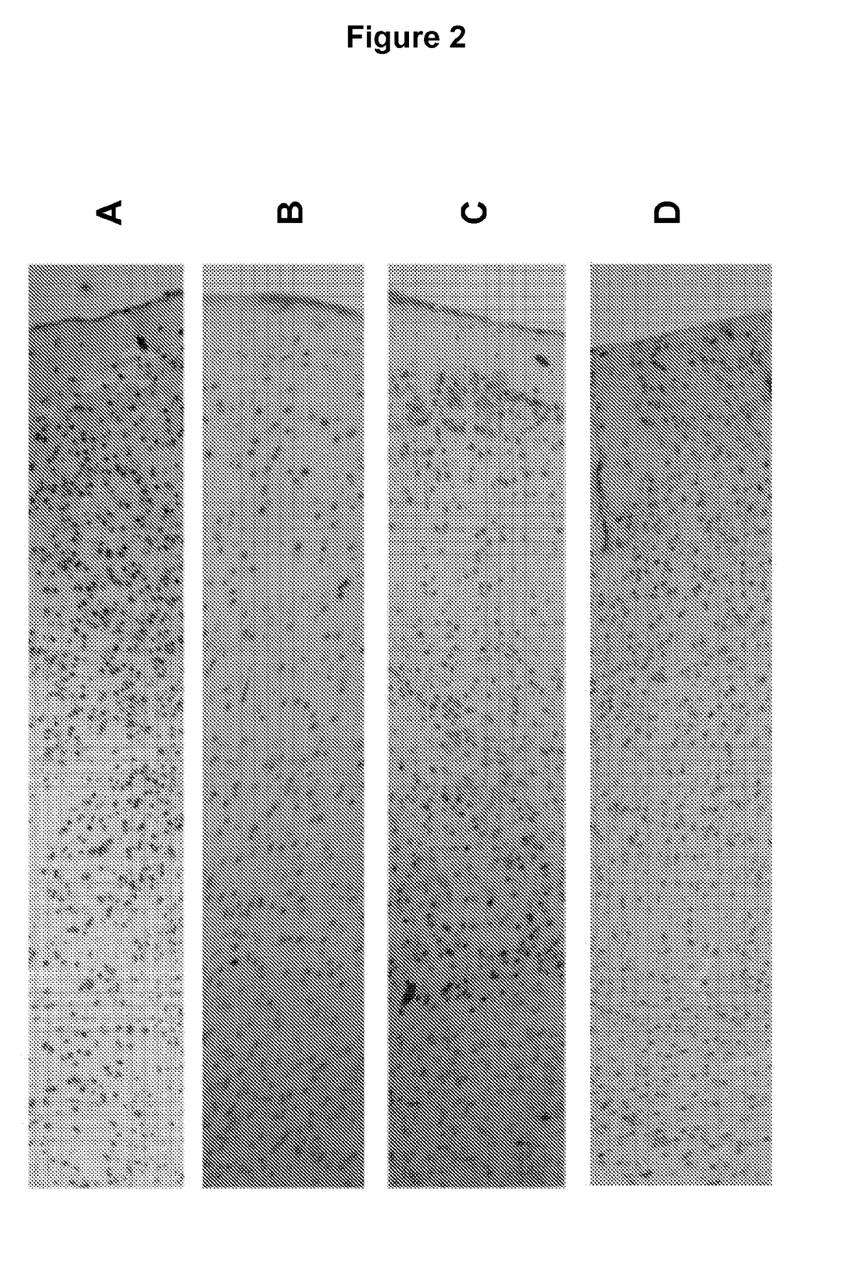
FIG. 2 describes the results of Immunohistochemical visualization of the phosphorylated form of CREB, pCREB (Ser133) in formalin fixed tissue from mouse cerebellum of samples after increasing time of incubations in room temperature following stabilization of the samples according to the method of the invention. Panel A 0 min, Panel B 15 min, Panel C 6 and Panel 24 hours following stabilization.

FIG. 2 describes the results of Immunohistochemical visualization of the phosphorylated form of CREB, pCREB (Ser133) in formalin fixed tissue from mouse cerebellum of samples after increasing time of incubations in room temperature following stabilization of the samples according to the method of the invention. Panel A 0 min, Panel B 15 min, Panel C 6 h, and Panel D 24 h following stabilization. pCREB positive nuclei can be seen through out the tissue even after 24 h incubation at room temperature after treatment evidencing complete stabilization of the sample.

What is claimed is:

1. A method for stabilizing a biological sample for analysis, the method comprising:
   a) extracting a biological sample from an organism;
   b) heating the sample to a temperature of at least about 70° C. within 3 minutes from the time of extraction of the sample from the organism to arrest enzymatic processes; and
   c) submitting the heated sample to chemical fixation.

2. The method according to claim 1, wherein the method is for stabilizing a biological sample for histological analysis.

3. The method according to claim 1, wherein the method further comprises analizing the fixed sample a histochemical assay and/or an immunohistochemical assay.

4. The method according to claim 1, wherein the biological sample comprises at least one protein having a post-translational modification.

5. The method according to claim 4, wherein the post-translational modification comprises phosphorylation.

6. The method according to claim 1, wherein the chemical fixation is performed using a cross-linking agent.

7. The method according to claim 6, wherein the cross-linking agent is an aldehyde.

8. The method according to claim 7, wherein the aldehyde is formaldehyde or glutaraldehyde.

9. The method of claim 1, wherein the sample is heated to a temperature of at least 70° C. within 2 minutes from the time of extraction of the sample from the organism.

10. The method of claim 1, wherein the sample is heated to a temperature of at least 70° C. within 2 minutes from initiation of heating.

11. The method of claim 1, wherein heating arrests at least 60% of enzymatic activity of the sample.

12. The method of claim 1, wherein heating arrests at least 70% of enzymatic activity of the sample.

13. The method of claim 1, wherein
   the sample comprises a plurality of biological macromolecules, the biological molecules comprising a primary structure; and
   heating degrades the primary structure of less than 5% of the plurality of biological macromolecules.

14. The method of claim 13, wherein heating degrades the primary structure of less than 2% of the plurality of biological macromolecules.

15. The method of claim 1, wherein heating comprises conduction, convection, or radiation.

16. The method of claim 1, wherein
   heating comprises conduction; and
   the biological sample comprises a shape such that no part of the sample is more than 1 cm from the source of conductive heat.

17. The method of claim 1, wherein heating comprises conduction;
   and the biological sample comprises a shape such that no part of the sample is more than 9 mm from the source of conductive heat.

18. The method of claim 1, wherein the sample is heated to a temperature of about 70° C. up to about 100° C.

19. The method of claim 1, wherein the sample is heated to a temperature of at least about 80° C.

20. The method of claim 1, further comprising:
   placing the extracted sample in a container prior to heating; and
   evacuating air from the container such that the sample directly contacts the container.

21. The method of claim 1, wherein the sample comprises a proteolytic enzyme.

22. The method of claim 1, wherein the sample comprises a tissue selected from the group consisting of tissue, muscle, bone, bone marrow, tooth, hair, skin, brain, kidney, liver, stomach, intestine, reproductive organ, and pancreas.

23. The method of claim 1, wherein the sample comprises a fluid selected from the group consisting of tears, saliva, blood, semen, sweat, and urine.

24. The method of claim 1, wherein the organism is selected from the group consisting of mammal, reptile, invertebrate, fish, insect, and bird.

25. The method of claim 1, wherein the organism is selected from the group consisting of human, primate, rabbit, sheep, dog, cat, horse, monkey, mouse, and rat.

* * * * *